US008151204B2

(12) United States Patent  (10) Patent No.: US 8,151,204 B2
Lusen et al.  (45) Date of Patent: Apr. 3, 2012

(54) DOCUMENT VIEWING AND MANAGEMENT SYSTEM

(75) Inventors: William D. Lusen, Merion Station, PA (US); Frank W. Racis, Spring City, PA (US); Kay L. Davis, Pottstown, PA (US); Margaret Eden, Chester Springs, PA (US); Jeffrey T. Phillips, Middletown, DE (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 743 days.

(21) Appl. No.: 11/945,584

(22) Filed: Nov. 27, 2007

(65) Prior Publication Data

US 2008/0126967 A1  May 29, 2008

Related U.S. Application Data

(60) Provisional application No. 60/867,608, filed on Nov. 29, 2006.

(51) Int. Cl.
*G06F 3/14* (2006.01)
*G06F 3/17* (2006.01)

(52) U.S. Cl. ............ 715/769; 715/230; 715/835; 705/2; 719/329; 358/1.13; 358/1.18

(58) Field of Classification Search .......... 715/200–277, 715/835; 700/701–866; 709/201–229; 705/50–79, 705/2; 345/30–111; 348/206–231.9; 358/1.18; 719/329

See application file for complete search history.

(56) References Cited

U.S. PATENT DOCUMENTS

| | | | |
|---|---|---|---|
| 6,262,732 B1 * | 7/2001 | Coleman et al. | 715/835 |
| 6,961,135 B1 | 11/2005 | Nakagiri et al. | |
| 6,999,198 B1 | 2/2006 | Nakagiri et al. | |
| 7,233,403 B2 | 6/2007 | Nakagiri et al. | |
| 7,426,057 B2 * | 9/2008 | Mori et al. | 358/1.18 |
| 7,688,459 B2 * | 3/2010 | Mori et al. | 358/1.13 |
| 2002/0011990 A1 | 1/2002 | Anwar | |
| 2004/0190057 A1 | 9/2004 | Takahashi et al. | |
| 2004/0194014 A1 | 9/2004 | Anwar | |
| 2004/0263907 A1 * | 12/2004 | Hiraki | 358/1.18 |
| 2005/0078974 A1 | 4/2005 | Uchida et al. | |
| 2005/0200870 A1 | 9/2005 | Nakagiri et al. | |
| 2006/0048043 A1 | 3/2006 | Kikuchi | |
| 2006/0080142 A1 * | 4/2006 | Hart et al. | 705/2 |
| 2007/0076984 A1 | 4/2007 | Takahashi et al. | |
| 2007/0268522 A1 * | 11/2007 | Miyamoto | 358/1.18 |
| 2008/0034381 A1 * | 2/2008 | Jalon et al. | 719/329 |
| 2010/0058166 A1 * | 3/2010 | Chikyu | 715/230 |

* cited by examiner

*Primary Examiner* — Ruay Ho
(74) *Attorney, Agent, or Firm* — Alexander J Burke (57) ABSTRACT

A document management and thumbnail image viewing system enables a user to display separate pages in individual different documents as well as to expand an image to view more detail in a single document, move pages across documents, and insert/delete pages or documents. A document management and viewing system includes a user interface for providing data representing a single composite display image including multiple reduced size images of individual pages of a first document and multiple reduced size images of individual pages of a different second document. The single composite display image includes at least one indicator identifying a transition between pages of the first and second documents and enables a user to select and move a page from the first document to the second document. A document processor updates stored data representing the first and second documents in response to a command entered using the single composite display image.

17 Claims, 8 Drawing Sheets

```
                    PAGE INFORMATION
    DOC TYPE      | TELEMET              ▽ |
    DOC DATE      | 7/13/2005 1:06:47 AM   |
    VERSION         1/1                              803
    VERSION DATE    7/13/2005 1:06:49 PM
805 BATCH #
    FOLDER        | 1066532894 (ENCOUNTER) ▽ |
    FOLDER NAME     BANGLE, ROSE THELMA
    ENCOUNTER NO. 1066532894
```

DOCUMENT VIEWING AND MANAGEMENT SYSTEM

This is a non-provisional application of provisional application Ser. No. 60/867,608 filed Nov. 29, 2006, by W. D. Lusen et al.

FIELD OF THE INVENTION

This invention concerns a document management and viewing system, including a user interface supporting user manipulation of pages in, and between, different documents.

BACKGROUND OF THE INVENTION

Known document viewing and management systems involving thumbnail image viewing displaying multiple pages of one or more documents in a user interface display image, are typically not user friendly and lack ease of use. Thumbnail Views provide the ability for a Document Management System (DMS) to present a set of documents as an array of small images, providing a means for a user of the system to visually identify documents and manipulate them in relation to each other. Known thumbnail image viewing systems fail to provide user friendly easy access and simplified workflow of operation and fail to provide comprehensive viewing functions. A system according to invention principles addresses these deficiencies and related problems.

SUMMARY OF THE INVENTION

A document management and thumbnail image viewing system enables a user to display separate pages in individual different documents, use a "document break bar" to provide a visual cue distinguishing which pages are grouped into single documents, access and manipulate documents as well as document identifiers and attributes through a one-touch pop-up window and provide one-touch access to document, page, and filing functions via controls implemented on a thumbnail image. A document management and viewing system includes a user interface for providing data representing a single composite display image including multiple reduced size (thumbnail) images of individual pages of a first document and multiple reduced size images of individual pages of a different second document. The single composite display image includes at least one indicator identifying a transition between pages of the first and second documents and enables a user to select and move a page from the first document to the second document. A document processor updates stored data representing the first and second documents in response to a command entered using the single composite display image.

DETAILED DESCRIPTION OF THE INVENTION

A document management and viewing system (referred to as a DMS) provides reduced size images (thumbnail views) representing a set of documents as an array of small images. This provides a simple means for a user of the system to visually identify documents and easily manipulate them in relation to each other. The DMS manipulations comprise expansion of an image to view more detail in a single document, move pages between different documents and insert/delete pages in documents or insert/delete a document as a whole. The DMS enables a user to display separate pages in individual different documents, use a "document break bar" to provide a visual cue distinguishing which pages are grouped into single documents, access and manipulate documents as well as document identifiers and attributes through a one-touch pop-up window and provide one-touch access to document, page, and filing functions via controls implemented on a thumbnail image.

The system includes a document processor. A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of, hardware, firmware, and/or software.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UT display images in response to signals received from the input devices. In this way, the user interacts with the display image using the input devices, enabling user interaction with the processor or other device. The functions and process steps (e.g., of FIG. 10) herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams. A document or record comprises a compilation of data in electronic form and is the equivalent of a paper document and may comprise a single, self-contained unit of information.

Figure 1:
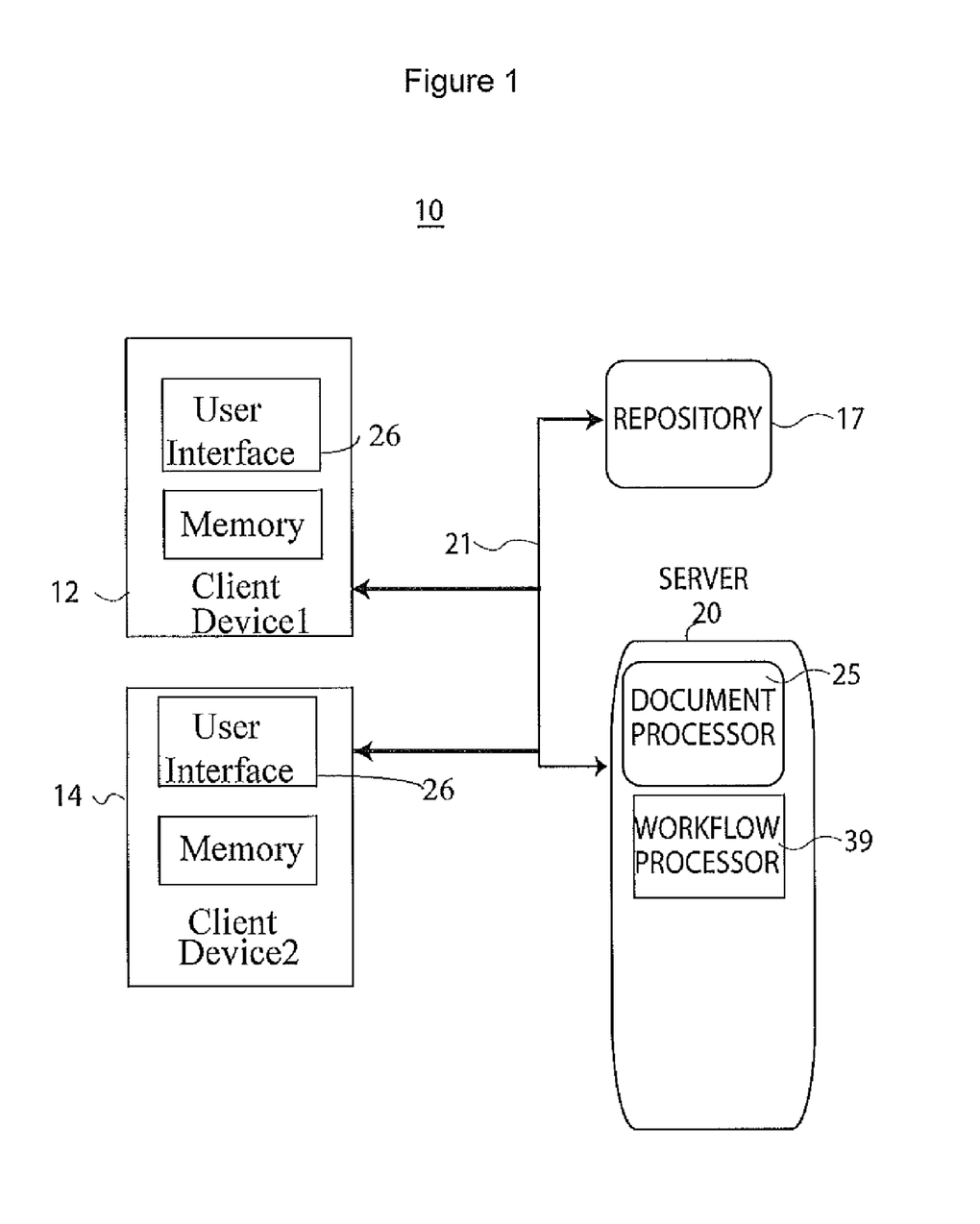
FIG. 1 shows a document management and viewing system, according to invention principles.

FIG. 1 shows a document management and viewing system 10 including client devices (workstations) 12 and 14, repository 17 and server 20 inter-communicating via network 21. User interface 26 provides data representing a single composite display image including multiple reduced size images of individual pages of a first document and multiple reduced size images of individual pages of a different second document. The composite display image includes at least one indicator identifying a transition between pages of the first and second documents and enabling a user to select and move a page from the first document to the second document. Document processor 25 updates stored data representing the first and second documents in response to a command entered using the single composite display image. The composite display image provides easy access and simplified workflow over functions used to manipulate documents, pages within documents, and the identifying attributes associated with those documents. Workflow processor 39 automatically adds a task to a worker task list upon detection of an update to a document or document attribute in response to user command or data entry made via the composite display image and image manipulation controls derived therefrom.

Figure 2:
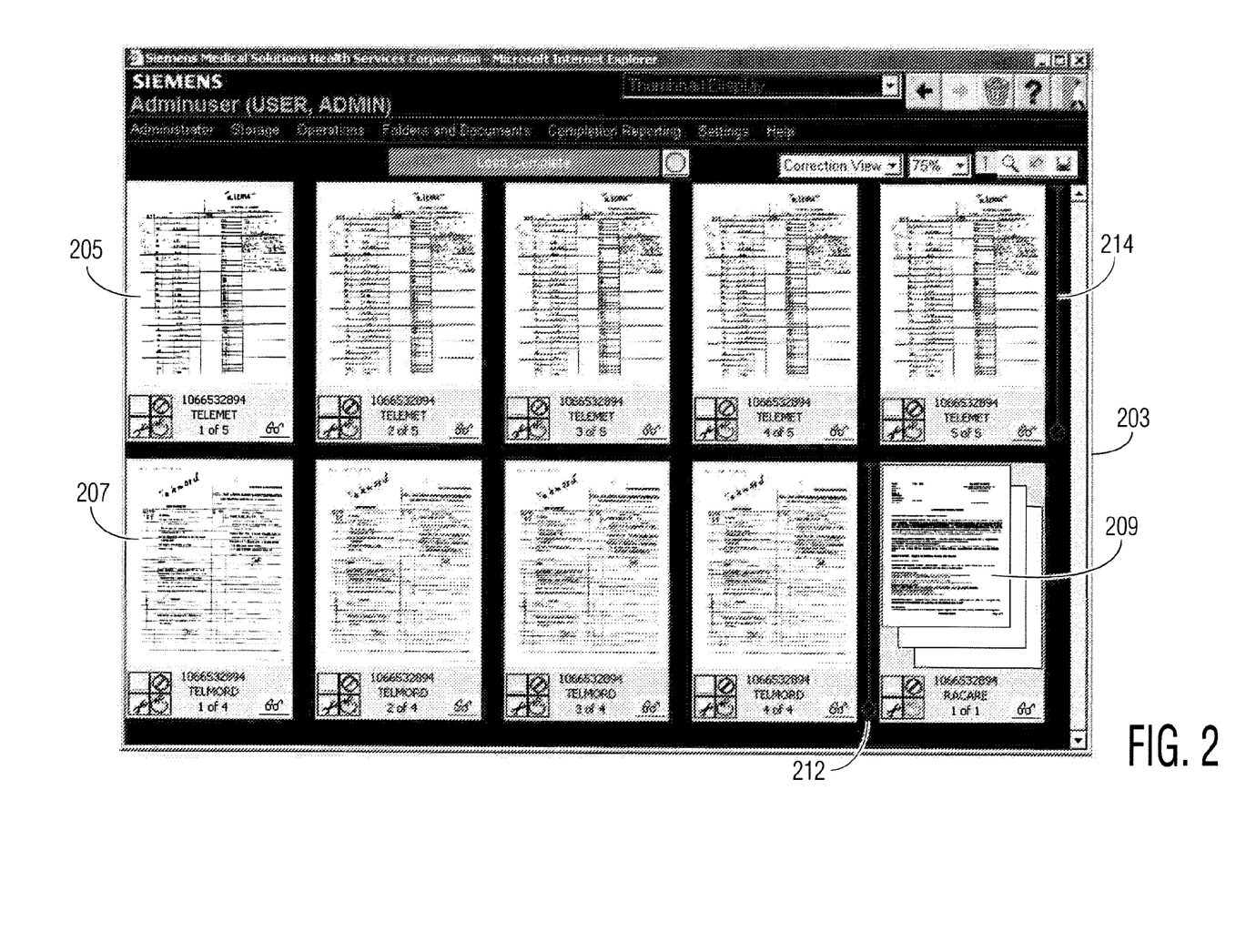
FIG. 2 shows a composite display image provided by a document management and viewing system, according to invention principles.
Figure 3:
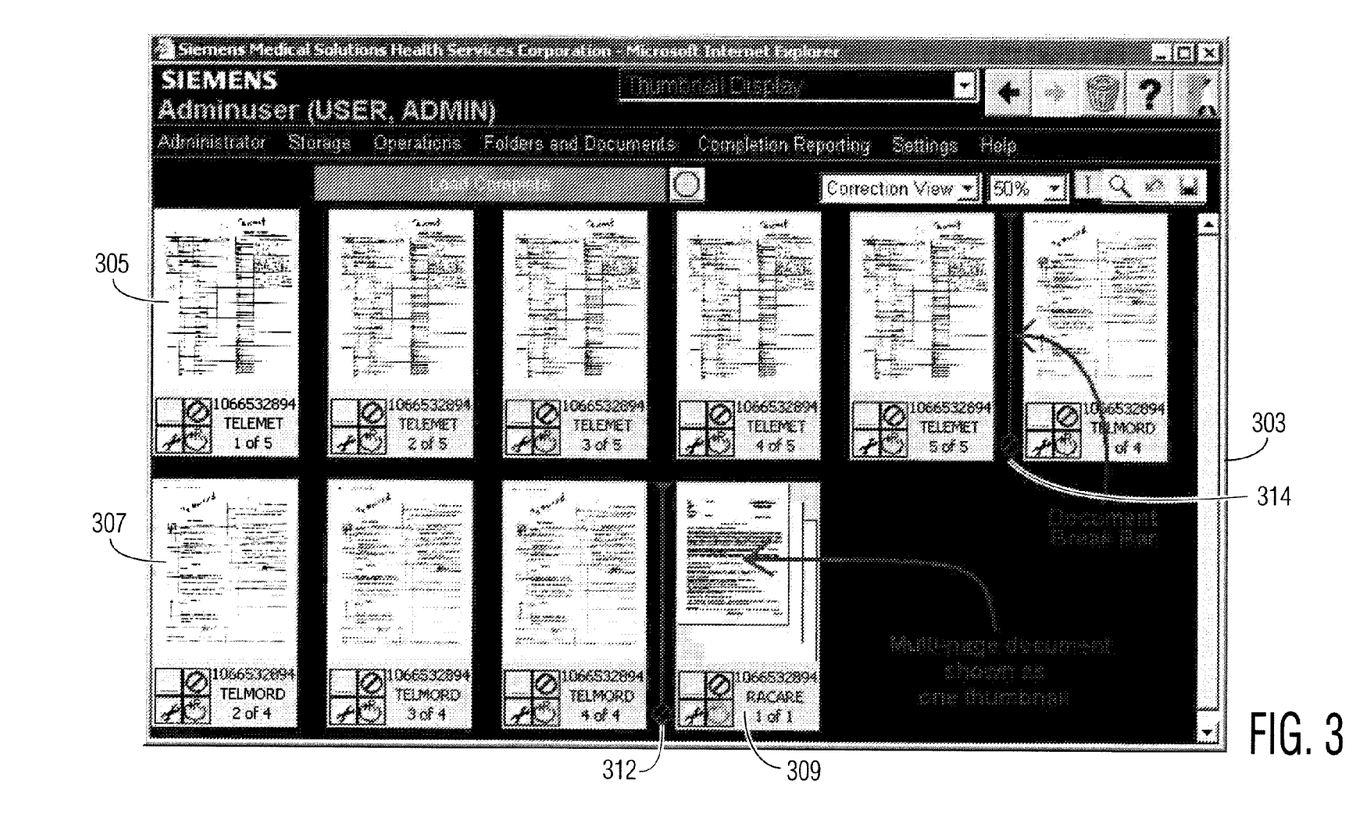
FIG. 3 shows a composite display image of three documents, according to invention principles.
Figure 4:
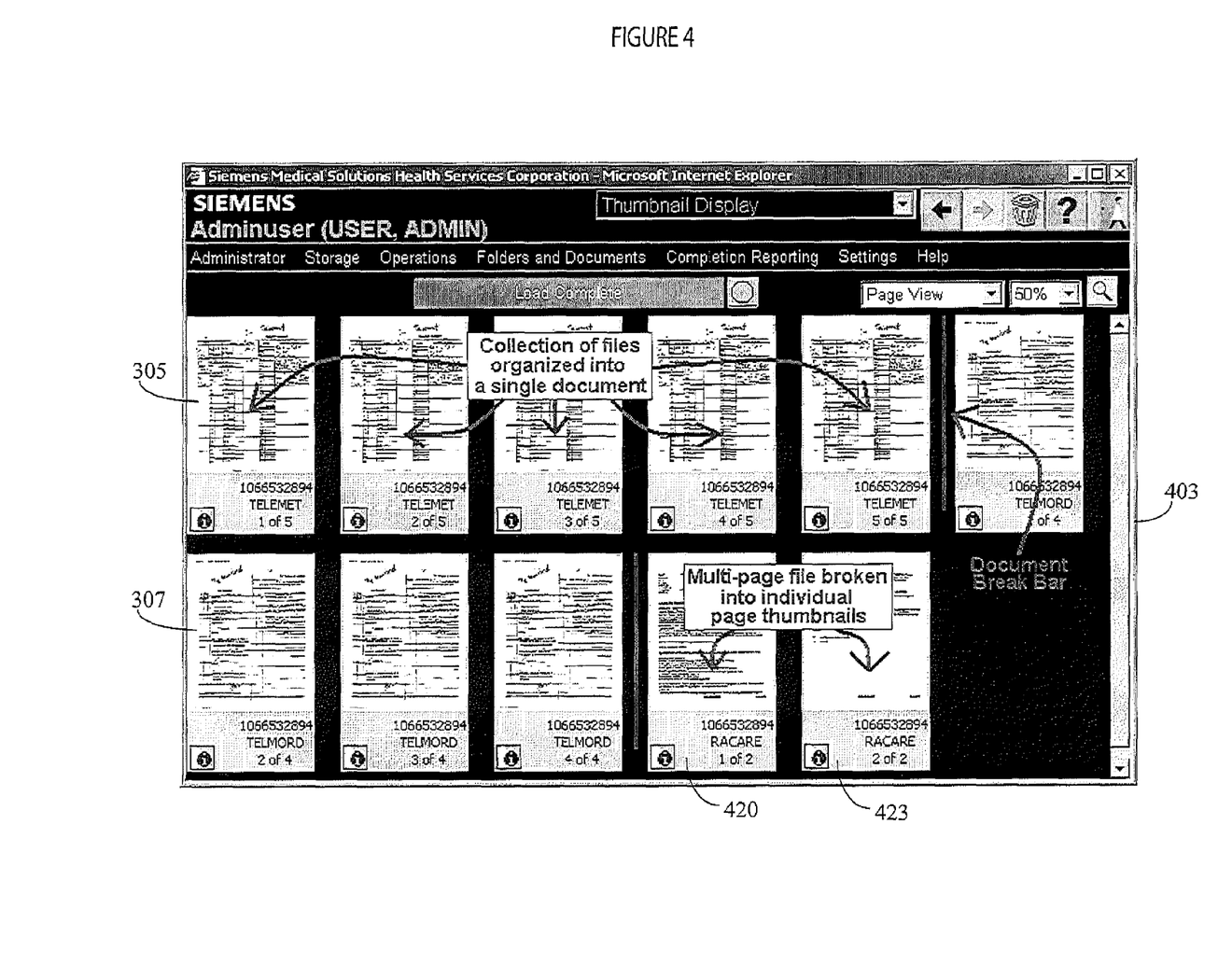
FIG. 4 shows the composite display image of FIG. 3 illustrating the last document comprising a single file with multiple pages being broken into individual reduced size images for each page, according to invention principles.

FIG. 2 shows composite display image 203 provided by a document management and viewing system (DMS) 10. Composite display image 203 provides individual break bars (212 and 214) to distinguish, visually, the grouping of pages into documents. A break bar indicates where one document ends and another begins. Composite display image 203 presents five individual pages of a first document 205 in the top half of image 203 prior to break bar 214. Four individual pages of a second document 207 are presented in the bottom half of image 203 prior to break bar 212. Following break bar 212, image 203 presents a multi-page view of a third document 209 in a reduced size image. FIG. 3 shows composite display image 303 presenting three documents in similar fashion to FIG. 2 but with a slightly different configuration in that six reduced size images are presented side by side in the top half of image 303. Composite display image 303 presents five individual pages of a first document (TELEMET) 305 in the top half of image 303 prior to break bar 314. Four individual pages of a second document (TELMORD) 307 are presented straddling the top and bottom half of image 303 prior to break bar 312. Following break bar 312, image 303 presents a multi-page view of a third document (RACARE) 309 (e.g. a multi-page TIF file) in a reduced size image. Thereby first document 305 consists of five individual reduced size images, the second document consists of four individual reduced size images and the third document consists of a single reduced size image with multiple pages. FIG. 4 shows the composite display image of FIG. 3 illustrating the third document 309 of FIG. 3 comprising a single file with multiple pages being broken into individual reduced size images 420 and 423. Further, composite display image 403 identifies five individual pages that comprise first document (TELEMET) 305 allowing direct navigation to individual pages within single document 305.

Figure 5:
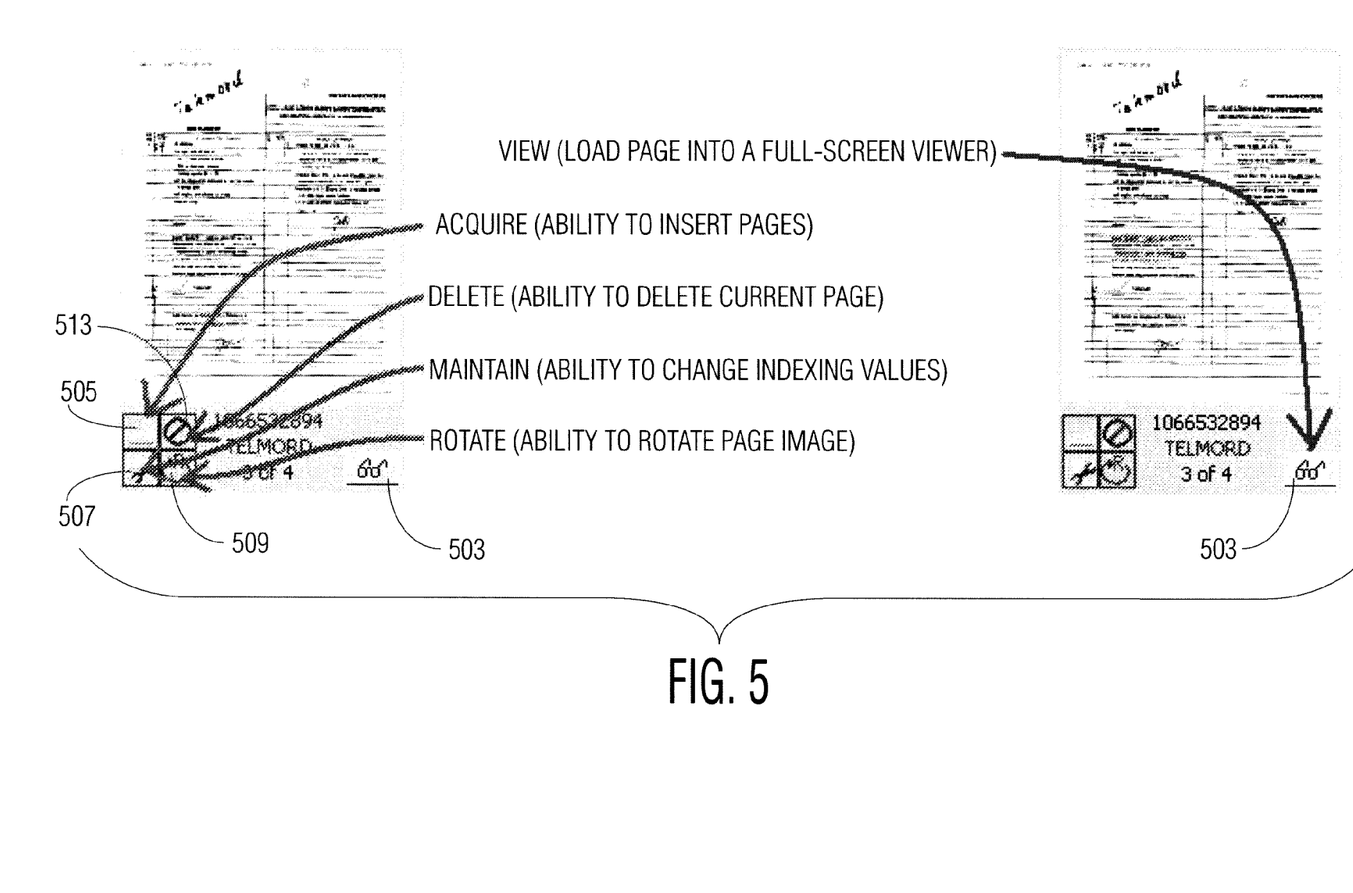
FIG. 5 illustrates image manipulation controls available on individual reduced size images, according to invention principles.
Figure 6:
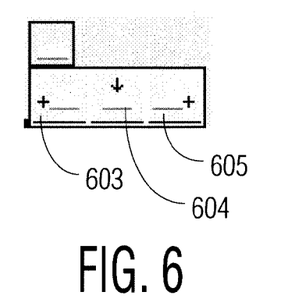
FIG. 6 illustrates a pop up toolbar provided in response to user selection of a button on a reduced size image, according to invention principles.

FIG. 5 illustrates image manipulation controls advantageously available on individual reduced size images comprising buttons for initiating functions and initiating presentation of toolbars for initiating functions that manipulate individual pages of a document and documents as a whole. The image manipulation controls are user friendly and their individual functions are visually obvious (and "self-educating"). Specifically, in response to user selection of button 503 on an individual reduced size image, the reduced size image is opened and expanded to a full size image using a viewer application and presented in a display screen of workstation 12 (FIG. 1). Thereby a user viewing multiple reduced size images of pages comprising a document in a composite display image is advantageously able to open and expand any individual page of the document and not just the first page of a document. FIG. 6 illustrates a pop up toolbar provided in response to user selection of button 505 FIG. 5 (an Acquire button) on a reduced size image. Buttons 603 and 605 (FIG. 6) enable a user to insert a new page in a document before and after a current page respectively. Button 604 enables a user to replace a current page in a document.

Figure 7:
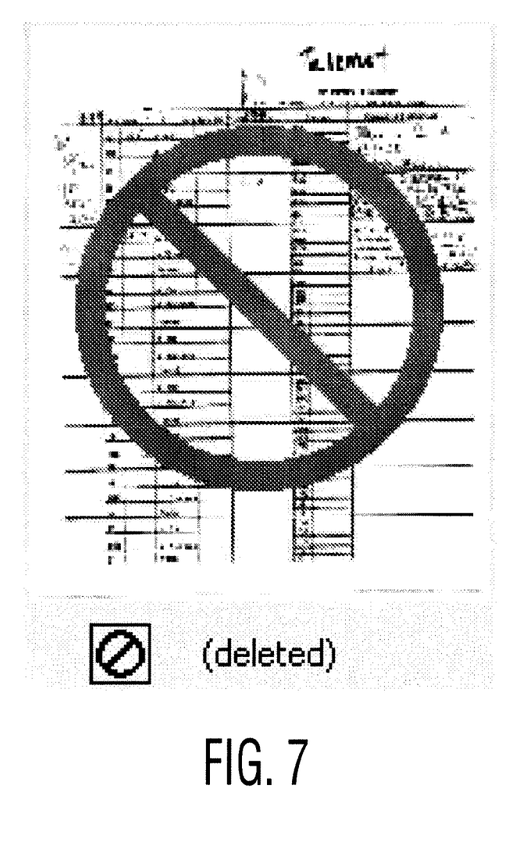
FIG. 7 shows the result of using a "Delete" control button, according to invention principles.

FIG. 7 shows the result of user selection of button 513 (Delete button) on an individual reduced size image. Specifically, in response to user selection of button 513 on an individual reduced size image, the image is temporarily deleted. The image is not deleted until the user either undoes the deletion or confirms changes via button selection within a single composite display image including multiple reduced size images of individual pages of a document.

Figure 8:
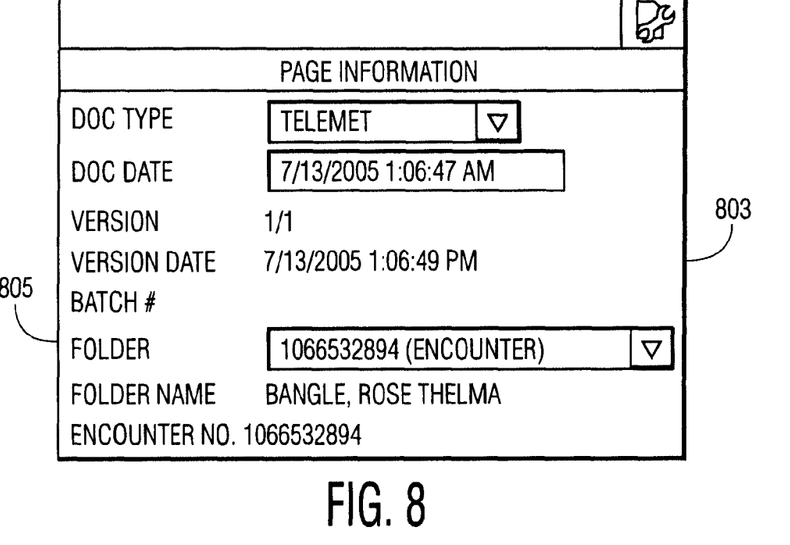
FIG. 8 shows a control button expanded into a pop-up image window that allows data entry changes to document index values, according to invention principles.

FIG. 8 illustrates popup image window 803 that allows data entry changes to document index values. The pop-up image window is provided in response to user selection of button 507 FIG. 5 (a Maintain button) on a reduced size image. In this embodiment, pop-up image window 803 allows data entry changes to document index values. An index is a single attribute or data element associated with a business object such as a document. An individual document in a Document Management System may have several indexes that are valued and identify the document. Some indexes are common to multiple documents such as the Document Type (DocType) or Document Date (DocDate). Other indexes associated with a document are inherited from a folder in which the document is filed. For example, if a document is filed in an Encounter folder, the document has an Encounter Number (EncNo), or if a document is filed in a MedRec folder, the document has a Medical Record Number (MedRecNo), or if a document is filed in an Employee folder, the document has an Employee Number (EmpNo).

In reduced size images in a composite display image (e.g., display image 403 of FIG. 4), a user may change the DocType, or DocDate via a pop-up index window from a reduced size image. A user may also change a folder in which a document is filed by changing the folder index associated with that document (e.g., changing the EncNo or MedRecNo, etc.) thereby the document is moved. A folder in which a document resides may be changed using data entry in a pop-up image window 803 accessed via a reduced size image which facilitates workflows that require re-filing of many documents involving performing data entry for one or more indexes. A user may also change the type of folder in which the document is filed by changing a Folder Type (FldType) associated with a document and specifying an appropriate folder index (e.g. changing the document from a MedRec folder to an Encounter folder by removing a MedRecNo and replacing it with an EncNo). Pop-up image window 803 enables a user to select document index values including, document type, document creation or last update date, document version, version date, batch number, folder identifier and name and encounter number. In other embodiments different index values may be used and edited. Further, folder data entry field 805 may be either an entered folder identifier or the folder can be selected from a list of pre-defined folders enabling a user to change a folder in which a document resides by data entry.

Figure 9:
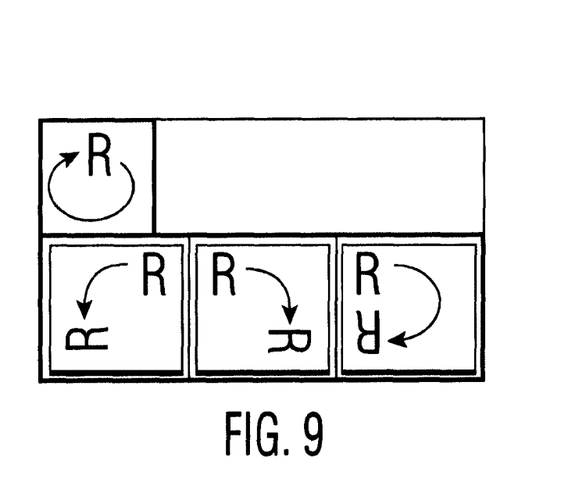
FIG. 9 illustrates a "Rotate" control that expands into a pop up toolbar, according to invention principles.

FIG. 9 illustrates a pop up toolbar providing a user selectable Rotate control. The pop up toolbar is provided in response to user selection of button 509 FIG. 5 (a Rotate button) on a reduced size image. Specifically, the rotate toolbar controls enable a user to rotate a document or page by ninety degrees in clockwise or anti-clockwise directions or by one hundred and eighty degrees. The system facilitates management of workflow of clinical, HIM (Healthcare Information Management) and business office personnel involving processes requiring access to, and manipulation of, documents and multimedia information. The system composite display image advantageously facilitates processes such as browsing the content of a patient record and batch acquisition of documents and provides quick access to documents easily identified by reduced size image. The composite display image also facilitates document/page correction processes (image manipulation, page re-ordering, document filing, etc.) because correction functions are easy to access through function buttons on a reduced size document image in a composite display image.

Figure 10:
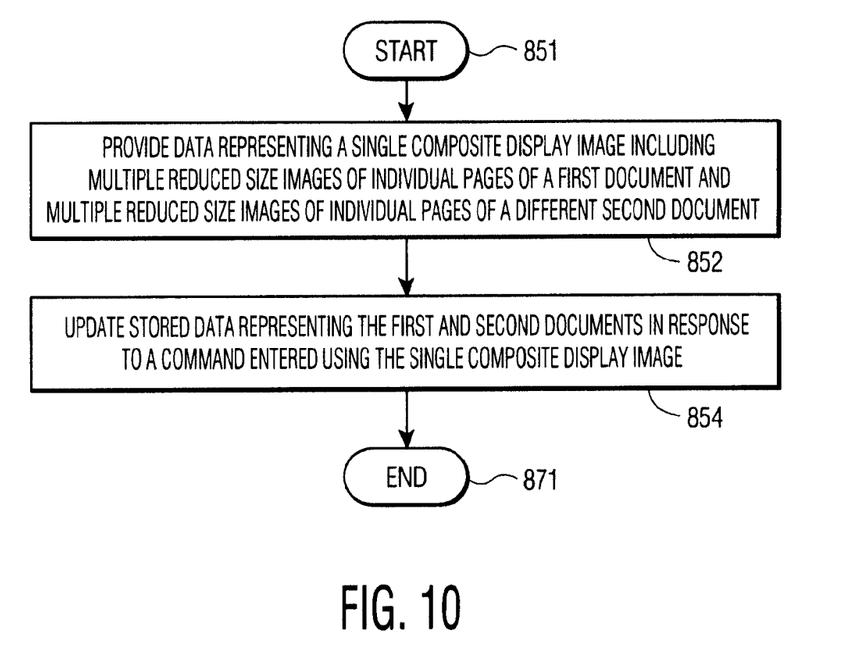
FIG. 10 shows a flowchart of a process used in a document management and viewing system, according to invention principles.

FIG. 10 shows a flowchart of a process used in document management and viewing system 10 (FIG. 1). In step 852 following the start at step 851, user interface 26 provides data representing a single composite display image including multiple reduced size images of individual pages of a first document and multiple reduced size images of individual pages of a different second document. The multiple reduced size images of individual pages of the first document are visually grouped in the single composite display image by being adjacent and the multiple reduced size images of individual pages of the second document are visually grouped in the single composite display image by being adjacent. The first and second documents are incorporated within corresponding different first and second folders and a user is able to move a first document from the first folder to the second folder in response to a command entered using the single composite display image. An individual reduced size image of a document includes buttons enabling a user to initiate presentation of an image menu. The image menu enables a user to change an index value associated with a document. Specifically, the image menu enables a user to change an index value comprising at least one of, (a) an Encounter number, (b) a Medical Record, (c) a Document Type and (d) a date number, associated with a document.

The single composite display image includes at least one indicator identifying a transition between pages of the first and second documents and enables a user to select and move a page from the first document to the second document. The single composite display image includes a further reduced size image comprising multiple individually selectable overlaid individual pages of a third document. A particular individual page of the individually selectable overlaid individual pages is presented in the foreground of the further reduced size image in response to user selection of the particular individual page. Also the single composite display image enables a user to insert a page into a document, delete a page from a document or expand and increase size of a user selected individual reduced size image of an individual page.

Individual reduced size images of individual pages include buttons enabling a user to initiate page manipulation commands on a page. The page manipulation commands include one or more of, (a) increasing a reduced size image page, (b) inserting a page into a document, (c) deleting a page from a document, (d) changing an index value associated with a document and (e) rotating a page. In step 854 document processor 25 updates stored data representing the first and second documents in response to a command entered using the single composite display image. Document processor 25 in response to user entry of at least one of (a) an Encounter number and (b) a Medical Record number, associated with a document, moves the document from one folder to a different folder (which may or may not be associated with a folder of a displayed document). Document processor 25 enables a user to add an indicator identifying a transition between portions of the first document and splitting the first document into two documents using the single composite display image. Workflow processor 39 automatically adds a task to a worker task list upon detection of an update to a document or document attribute in response to user command or data entry made via the composite display image. The process of FIG. 10 terminates at step 871.

The systems and processes of FIGS. 1-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 is usable in any field to provide the composite display image in eluding reduced size images of individual pages of a document in a Document Management System in any industry. The processes and applications may in alternative embodiments, be located on one or more (e.g., distributed) processing devices accessing a network linking the elements of FIG. 1. Further, any of the functions and steps provided in FIGS. 1-10 may be implemented in hardware, software or a combination of both and may reside on one or more processing devices located at any location of a network linking the elements of FIG. 1 or another linked network including the Internet.

What is claimed is:

1. A document management and viewing system, comprising:
    a user interface for providing data representing a single composite display window concurrently displaying pages of different first and second documents as a plurality of non-overlaid reduced size images of individual pages of the first document and a plurality of non-overlaid reduced size images of individual pages of the different second document and,
        including at least one document break element identifying a transition between pages of said first and second documents and providing a visual cue distinguishing pages grouped into single documents,
        enabling a user to select and move a page from said first document to a desired location within said second document visually separated from said first document by said document break element and
        updating stored data representing said first and second documents in response to a command entered using said single composite display window, said single composite display window enabling a user to expand and increase size of a user selected individual reduced size image of an individual page.

2. A system according to claim 1, wherein
said single composite display window includes a further reduced size image comprising a plurality of individually selectable overlaid individual pages of a third document and enables a user to select and move a page from said first document across said document break element to said second document.

3. A system according to claim 2, wherein
a particular individual page of said individually selectable overlaid individual pages is presented in the foreground of said further reduced size image in response to user selection of said particular individual page.

4. A system according to claim 1, wherein
said first and second documents are incorporated within corresponding different first and second folders and a user is able to move a first document from said first folder to said second folder in response to a command entered using said single composite display window.

5. A system according to claim 1, wherein
an individual reduced size image of a document includes buttons enabling a user to initiate page manipulation commands on a page displayed in said individual reduced size image.

6. A system according to claim 5, wherein
said page manipulation commands include at least two of, (a) increasing a reduced size image page, (b) inserting a page into a document, (c) deleting a page from a document, (d) changing an index value associated with a document and (e) rotating a page.

7. A system according to claim 1, wherein
said plurality of reduced size images of individual pages of said first document are visually grouped in said single composite display window by being adjacent.

8. A system according to claim 7, wherein
said plurality of reduced size images of individual pages of said second document are visually grouped in said single composite display window by being adjacent.

9. A system according to claim 1, wherein
an individual reduced size image of a document includes buttons enabling a user to initiate presentation of an image menu enabling a user to change an index value associated with a document.

10. A system according to claim 9, wherein
said system generates said image menu to enable a user to change an index value comprising at least one of, (a) an Encounter number and (b) a Medical Record number, associated with a document.

11. A system according to claim 10, wherein
said system generates said image menu to enable a user to change an index value comprising at least one of, (a) a Document Type and (b) a date, associated with a document.

12. A system according to claim 10, wherein
said document processor in response to user entry of at least one of, (a) an Encounter number and (b) a Medical Record number, associated with a document, moves said document from one folder to a different folder.

13. A system according to claim 1, wherein
a user is able to move a first document from said first folder to a folder not referenced by any folder associated with displayed documents.

14. A document management and viewing system, comprising:
    a user interface for providing data representing a single composite display window concurrently displaying pages of different first and second documents as a plurality of non-overlaid reduced size images of individual pages of the first document and a plurality of non-overlaid reduced size images of individual pages of the different second document and,
        including at least one document break element identifying a transition between pages of said first and second documents and providing a visual cue distinguishing pages grouped into single documents,
        enabling a user to select and move a page from said first document to a desired location within said second document visually separated from said first document by said document break element and
    updating stored data representing said first and second documents in response to a command entered using said single composite display window, said single composite display window enabling a user to insert a page into a document, delete a page from a document or replace a page in a document.

15. A document management and viewing system, comprising:
    a user interface for providing data representing a single composite display window concurrently displaying pages of different first and second documents as a plurality of non-overlaid reduced size images of individual pages of the first document and a plurality of non-overlaid reduced size images of individual pages of the different second document and said plurality of reduced size images of individual pages of said first document are visually grouped in said single composite display window by being adjacent and said plurality of reduced size images of individual pages of said second document are visually grouped in said single composite display window by being adjacent and, including at least one document break element identifying a transition between pages of said first and second documents and providing a visual cue distinguishing pages grouped into single documents and enabling a user to select and move a page from said first document to a desired location within said second document visually separated from said first document by said document break element, individual reduced size images of individual pages include buttons enabling a user to initiate page manipulation commands on a page and updating stored data representing said first and second documents in response to a command entered using said single composite display window.

16. A system according to claim 15, wherein said single composite display window and enables a user to select and move a page from said first document across said document break element to said second document, access and manipulate documents, document identifiers and attributes and said page manipulation commands include at least two of, (a) increasing a reduced size image page, (b) inserting a page into a document, (c) deleting a page from a document, (d) changing an index value associated with a document and (e) rotating a page.

17. A system according to claim 15, wherein said document processor enables a user to add an indicator identifying a transition between portions of said first document and splitting said first document into two documents using said single composite display window.

\* \* \* \* \*